United States Patent [19]

Nèdelèc et al.

[11] 4,130,658
[45] Dec. 19, 1978

[54] NOVEL PHENETHYLAMINES

[75] Inventors: Lucien Nèdelèc, Le Raincy; Daniel Fréchet, Paris; Claude Dumont, Nogent-sur-Marne, all of France

[73] Assignee: Roussel Uclaf, Paris, France

[21] Appl. No.: 809,810

[22] Filed: Jun. 24, 1977

[30] Foreign Application Priority Data

Jul. 1, 1976 [FR] France .................. 76 20140

[51] Int. Cl.² .................. A61K 31/135; C07C 87/28; C07C 69/02; C07C 69/78
[52] U.S. Cl. .................. 424/308; 424/311; 424/330; 560/108; 560/138; 260/570.8 R
[58] Field of Search .................. 260/570.8 R; 560/8, 560/250, 108, 138; 424/311, 330, 308

[56] References Cited

PUBLICATIONS

Kakac, Ernest B. et al. "Synthetic experiments in the group of hypotensive alkaloids." Collection Czech. Chem. Commun. 29, 251–265 (1964).
Martirosyan, G. T. et al. "Synthesis and reactions of beta, gamma-unsaturated amines." Zh. Org. Khim. (1970), 6(3), 446–449.

Primary Examiner—James O. Thomas, Jr.
Assistant Examiner—Leah Hendriksen
Attorney, Agent, or Firm—Hammond & Littell

[57] ABSTRACT

Novel phenethylamines of the formula

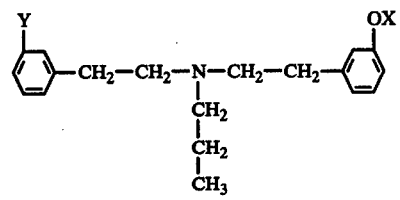

wherein X is selected from the group consisting of hydrogen, acyl of an aliphatic carboxylic acid of 2 to 6 carbon atoms and benzoyl and Y is selected from the group consisting of hydrogen and —OX and their non-toxic, pharmaceutically acceptable acid addition salts having dopaminergic stimulating activity and their preparation and novel intermediates.

21 Claims, No Drawings

NOVEL PHENETHYLAMINES

OBJECTS OF THE INVENTION

It is an object of the invention to provide the novel phenethylamines of formula I and their non-toxic, pharmaceutically acceptable acid addition salts.

It is another object of the invention to provide a novel process for the preparation of compounds of formula I and to novel intermediates therefore.

It is a further object of the invention to provide novel dopaminergic stimulating compositions and to a novel method of treating the symptoms of Parkinson disease in warm-blooded animals.

These and other objects and advantages of the invention will become obvious from the following detailed description.

THE INVENTION

The novel compounds of the invention are selected from the group consisting of phenethylamines of the formula

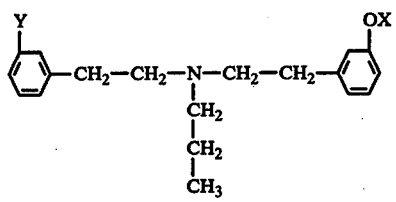

wherein X is selected from the group consisting of hydrogen, acyl of an aliphatic carboxylic acid of 2 to 6 carbon atoms and benzoyl and Y is selected from the group consisting of hydrogen and —OX and their non-toxic, pharmaceutically acceptable acid addition salts. Among the preferred compounds of the invention, Y is hydrogen.

Examples of acids for the acyl of aliphatic carboxylic acids of 2 to 6 carbon atoms are alkanoic acids such as acetic acids, propionic acid, n-butyric acid, isobutyric acid, n-valeric acid and pivaloic acid.

Examples of suitable acids for the formation of non-toxic, pharmaceutically acceptable acid addition salts are inorganic acids such as hydrochloric acid, hydrobromic acid, hydroiodic acid, nitric acid, sulfuric acid, or phosphoric acid; organic acids such as acetic acid, formic acid, benzoic acid, maleic acid, formic acid, succinic acid, tartaric acid, citric acid, oxalic acid, glyoxylic acid or asparatic acid, alkane sulfonic acids such as methane sulfonic acid and aryl sulfonic acids such as benzene sulfonic acid.

Among the preferred compounds of formula I are those where X is hydrogen, acetyl or benzoyl and Y is hydroxyl when X is hydrogen or Y is acetoxy when X is acetyl or Y is benzoyloxy when X is benzoyl and their non-toxic, pharmaceutically acceptable acid addition salts. Also preferred are the compounds of formula I wherein Y is hydrogen and X is hydrogen, acetyl or benzoyl and their acid addition salts.

The novel process of the invention for the preparation of compounds of formula I comprises hydrolyzing a compound of the formula

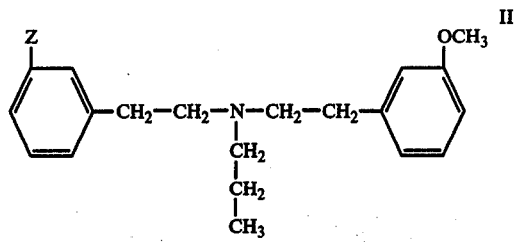

wherein Z is hydrogen or methoxy to obtain a compound of the formula

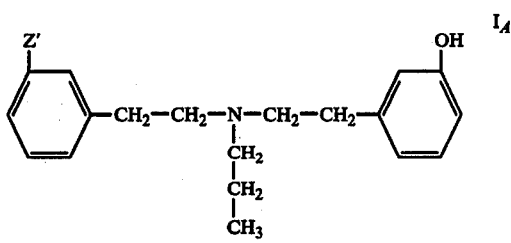

wherein Z' is hydrogen or hydroxy which may be isolated and if desired salified or may be reacted with an acid halide of the formula $$X'-Hal \qquad III$$

wherein X' is benzoyl or acyl of an aliphatic carboxylic acid of 2 to 6 carbon atoms or with an acid anhydride of the formula $(X')_2O$ to obtain a compound of the formula

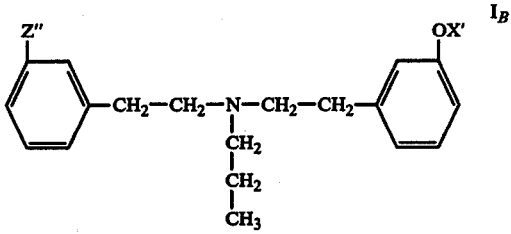

wherein X' has the above definition and Z'' is hydrogen or OX' which, if desired may be salified. Preferably Y, Z, Z' and Z'' are hydrogen.

In a preferred mode of the process, the hydrolysis of the compound of formula II is effected at reflux with concentrated hydrobromic acid. When X' is acyl of an aliphatic carboxylic acid of 2 to 6 carbon atoms, the reaction of the acid halide with a compound of formula $I_A$ is effected in the presence of a strong acid such as trifluoroacetic acid and when X' is benzoyl, the reaction of the acid halide is preferably effected in an organic solvent such as benzene in the presence of an amine such as triethylamine. If the acid anhydride is used, the reaction is preferably effected at room temperature in the presence of an alkali metal acetate such as sodium acetate.

The acid addition salts of the compounds of formula I may be formed by known methods by reacting substantially stoichiometric amounts of the acid and the base of formula I.

The novel dopaminergic stimulating compositions of the invention are comprised of a dopaminergically effective amount of at least one compound selected from the group consisting of a compound of formula I and its non-toxic, pharmaceutically acceptable acid addition salts and an inert pharmaceutical carrier. The compositions may be in the form of tablets, dragees, gelules, capsules, granules, suppositories and injectable solutions or suspensions.

Examples of suitable excipients or pharmaceutical carriers are talc, arabic gum, lactose, starch, magnesium stearate, cacao butter, aqueous and non-aqueous vehicles, fatty bodies of animal or vegetable origin, paraffinic derivatives, glycols, preservatives, diverse wetting agents, emulsifiers or dispersants.

The compositions of the invention possess remarkable susceptible dopaminergic properties making them useful for treating neurological syndromes of extrapyramidal origin. They are useful for the treatment of the symptoms of Parkinson disease, treatment of postencephalitic parkinson syndromes and of arteriosclerous origin or toxic etiology.

Among the preferred compositions of the invention are those where X is hydrogen, acetyl or benzoyl and Y is hydroxyl when X is hydrogen or Y is acetoxy when X is acetyl or Y is benzoyloxy when X is benzoyl and their non-toxic, pharmaceutically acceptable acid addition salts. Also preferred are the compounds of formula I wherein Y is hydrogen and X is hydrogen, acetyl or benzoyl and their acid addition salts.

The novel method of the invention for treating the syndromes of Parkinson disease in warm-blooded animals including humans comprises administering to warm-blooded animals a dopaminergically effective amount of at least one compound of formula I and its non-toxic, pharmaceutically acceptable acid addition salts. The compounds may be administered orally, rectally or parenterally and the usual daily dose is 0.2 to 10 mg/kg by oral route in man.

The compounds of formula II wherein Z is hydrogen may be prepared by reacting a compound of the formula

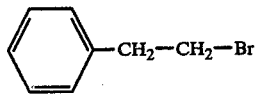

IV with 3-methoxyphenethylamine to obtain a compound of the formula

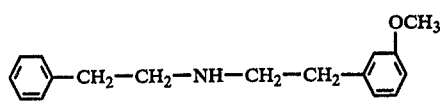

V which is then reacted with a propyl halide such as the chloride, bromide or iodide to obtain the corresponding compound of formula II.

The compounds of formula II wherein Z is methoxy may be prepared by reducing a compound of the formula

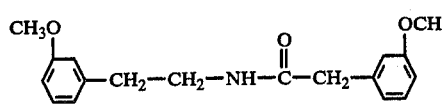

IV with diborane in tetrahydrofuran to obtain a compound of the formula

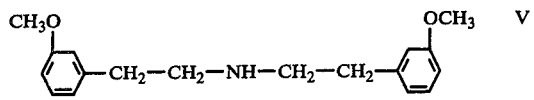

V which is then reacted with a propyl halide as before to obtain the corresponding compound of formula II.

In the following examples there are described several preferred embodiments to illustrate the invention. However, it should be understood that the invention is not intended to be limited to the specific embodiments.

EXAMPLE 1

3-[2-{(N-phenethyl) (N-propyl)-amino}ethyl]- phenol hydrochloride

STEP A: N-phenethyl-3-methoxyphenethylamine

A mixture of 1.51 g of β-(3-methoxyphenyl)-ethylamine and 1.85 g of β-phenethyl bromide was heated to 70°-80° C. on a bath and then was progressively heated to 165° C. over 10 minutes. The mixture was held at 165° C. for 5 minutes and was then cooled. 50 ml of water and then 4 ml of concentrated ammonium hydroxide were added thereto and the mixture was extracted 3 times with 40 ml of methylene chloride. The combined organic extracts were washed with 100 ml of aqueous sodium chloride solution and was dried over magnesium sulfate and was filtered. The filtrate was evaporated to dryness to obtain 3.4 g of raw product which was chromatographed over silica gel. Elution was with a 9-1 chloroform-ethanol mixture and the homogeneous fraction with an Rf = 0.45 was taken to obtain 1.2 g of N-phenethyl-3-methoxyphenethylamine in the form of a yellow oil.

STEP B: N-phenethyl-N-propyl-3-methoxyphenethylamine 1.1 ml of propyl iodide and 1.1 g of potassium carbonate were added to a solution of 1.1 g of the product of Step A in 15 ml of acetone and the mixture was refluxed with stirring for 5 hours. The acetone was distilled under reduced pressure and 50 ml of water were added thereto. The mixture was extracted 3 times with 20 ml of methylene chloride and the combined organic phases were washed with 70 ml of aqueous sodium chloride solution. The organic phases were dried over magnesium sulfate, filtered and evaporated to dryness under reduced pressure to obtain 1.25 g of N-phenethyl-N-propyl-3-methoxyphenethylamine in the form of an orange oil.

STEP C: 3-[2-{(N-phenethyl) (N-propyl)-amino}-ethyl]-phenolhydrochloride

A mixture of 1.25 g of the product of Step B in 10 ml of 48% hydrobromic acid was refluxed with stirring for 30 minutes and was then evaporated to dryness. 50 ml of water and 5 ml of concentrated ammonium hydroxide solution were added thereto and the mixture was extracted 3 times with 20 ml of methylene chloride. The combined organic extracts were washed with 50 ml of aqueous sodium chloride solution, were dried over magnesium sulfate and evaporated to dryness under reduced pressure. The 1.20 g of raw product was chromatographed over silica gel and was eluted with a 9-1 chloroform-methanol mixture to recover the fraction with an Rf = 0.40 for 700 mg of 3-[2-{(N-phenethyl)

(N-propyl)-amino}ethyl]-phenol in the form of a colorless oil.

1 ml of a solution of ethyl acetate saturated with dry hydrogen chloride was added to a solution of the phenol in 2 ml of isopropanol and crystallization was started. The mixture stood at room temperature for 30 minutes and was vacuum filtered. The recovered product was washed with ethyl acetate and with ether to obtain 650 mg of 3-[2-{(N-phenethyl) (N-propyl)-amino}ethyl]-phenol hydrochloride in the form of colorless cyrstals melting at 165° C.

Analysis: $C_{19}H_{25}NO \cdot HCl$; molecular weight = 319.86

| | % C 71.34 | % H 8.19 | % N 4.38 | % Cl 11.09 |
|---|---|---|---|---|
| Calculated: | 71.34 | 8.19 | 4.38 | 11.09 |
| Found: | 71.1 | 8.1 | 4.3 | 11.3 |

EXAMPLE 2

Acetate of 3-[2-{(N-phenethyl) (N-propyl)-amino}-ethyl]-phenol hydrochloride 4 ml of acetyl chloride were added over 5 minutes at 20°–25° C. to a solution of 8 g of the hydrochloride of Example 1 in 32 ml of trifluoroacetic acid and the mixture stood for 15 minutes with stirring. The mixture was evaporated to dryness under a pressure of 5 mm Hg at 30°–35° C. and the oily residue was dissolved in ethyl acetate. The solution was washed with water, with aqueous sodium bicarbonate and then water, was dried and evaporated to dryness to obtain 10 g of the acetate of 3-[2-{(N-phenethyl) (N-propyl)-amino}-ethyl]-phenol in the form of an almost colorless oil.

The 10 g of product were dissolved in 10 ml of ethyl acetate and an excess of ethyl acetate saturated with hydrochloric acid was added thereto. Crystallization was started and the mixture was iced and vacuum filtered. The recovered product was washed with iced ethyl acetate to obtain 7.5 g of the acetate of 3-[2-{(N-phenethyl) (N-propyl)-amino}-ethyl]-phenol hydrochloride in the form of a white solid melting at 110° C.

Analysis: $C_{21}H_{27}NO_2 \cdot HCl$; molecular weight = 361.91

| | % C 69.69 | % H 7.80 | % N 3.87 | % Cl 9.80 |
|---|---|---|---|---|
| Calculated: | 69.69 | 7.80 | 3.87 | 9.80 |
| Found: | 69.6 | 7.8 | 3.8 | 9.9 |

EXAMPLE 3

Fumarate of the benzoate of 3-[2-{(N-phenethyl) (N-propyl)-amino}-ethyl]-phenol 4.35 ml of benzoyl chloride were added at 20 to 25° C. under nitrogen to a suspension of 6 g of the hydrochloride of Example 1 in 60 ml of benzene and 9 ml of triethylamine and the mixture was evaporated to dryness at a pressure of 5 mm Hg at 35° C. The residue was taken up in water and the aqueous solution was extracted with ether. The ether phase was washed with water, with aqueous sodium bicarbonate solution and again with water, was dried and evaporated to dryness to obtain 9.3 g of raw product. The said product was chromatographed over silica gel and was eluted with methylene chloride and then with methanol. The homogenous fractions with an Rf = 0.33 (95-5 methylene chloride-ethanol) were combined and were evaporated to dryness to obtain 8 g of the benzoate of 3-[2-{(N-phenethyl)-(N-propyl)-amino}-ethyl]-phenol in the form of an oil.

The said product and 2.1 g of fumaric acid were dissolved in 30 ml of ethyl acetate at 60° C. and the mixture was filtered and crystallization was started. The mixture was refrigerated for 12 hours and was then vacuum filtered. The recovered product was washed with iced ethyl acetate to obtain 4.5 g of raw formate which was dissolved in 15 ml of ethyl acetate at 50° C. Crystallization was effected and after standing in the refrigerator for 12 hours, the mixture was vacuum filtered. The recovered product was washed with ether and dried at 30° C. under reduced pressure to obtain 3.2 g of the fumarate of the benzoate of 3-[2-{(N-phenethyl) (N-propyl)-amino}-ethyl]-phenol in the form of a white solid melting at 88° C.

Analysis: $C_{26}H_{29}NO_2 \cdot C_4H_4$; molecular weight = 503.57

| | % C 71.55 | % H 6.61 | % N 2.78 |
|---|---|---|---|
| Calculated: | 71.55 | 6.61 | 2.78 |
| Found: | 71.2 | 6.8 | 2.6 |

EXAMPLE 4

3,3'-(propylimino-di-2,1-ethanediyl)-bis-phenol

STEP A:
3-methoxy-N-[2-(3-methoxyphenyl)-ethyl]-benzene ethanamine hydrochloride A solution of 11.3 g of 3-methoxy-N-[2-(3-methoxyphenyl)-ethyl]-benzeneacetamide [Soc., 1927, p. 2270] in 200 ml of anhydrous tetrahydrofuran was refluxed and for 2 hours diborane prepared from 17 g of sodium borohydride and 85 ml of a complex of boron trifluoride-ether complex in diglyme was bubbled therethrough. At the end of the reaction, a gelatinous precipitate was observed and the mixture was then iced. 80 ml of water and then 40 ml of fuming hydrochloric acid were slowly added thereto and the mixture was refluxed for 1 hour. The tetrahydrofuran was removed by distillation and the mixture was made alkaline with 50 ml of sodium hydroxide. The mixture was extracted with methylene chloride and the organic extracts were washed with water, dried and evaporated to dryness to obtain 11.4 g of product. The latter was dissolved in 30 ml of ethyl acetate and an excess of hydrogen chloride in ethyl acetate was added thereto. The mixture was iced for 1 hour and was then vacuum filtered. The recovered product was washed with iced ethyl acetate and dried to obtain 8 g of 3-methoxy-N-[2-(3-methoxyphenyl)-ethyl]-benzene-ethanamide hydrochloride in the form of colorless platelets melting at 160° C.

Analysis: $C_{18}H_{23}NO_2 \cdot HCl$; molecular weight = 321.86

| | % C 67.17 | % H 7.52 | % N 4.35 | % Cl 11.02 |
|---|---|---|---|---|
| Calculated: | 67.17 | 7.52 | 4.35 | 11.02 |
| Found: | 67.0 | 7.8 | 4.3 | 11.3 |

STEP B:
3-methoxy-N-[2-(3-methoxyphenyl)-ethyl]-N-propyl-benzene-ethanamine A suspension of 8.75 g of the product of Step A, 17.5 g of calcined neutral potassium carbonate, 17.5 g of propyl iodide and 180 ml of acetone was refluxed for 6½ hours under nitrogen and the mixture was then filtered. The filtrate was evaporated to dryness and the residue was taken up in ether. The ether solution was washed with water, dried and evaporated to dryness to obtain 8.3 g of 3-methoxy-N-[2-(3-methoxyphenyl)-ethyl]-N-propyl-benzene-ethanamine which was used as is for the next step.

STEP C:
3,3'-(propylimino-di-2,1-ethanediyl)-bis-phenol

A solution of 8.3 g of the product of Step B in 80 ml of 48% hydrobromic acid was refluxed for an hour under nitrogen and the mixture was then iced. 120 ml of concentrated ammonium hydroxide were then added slowly thereto and the mixture was extracted with methylene chloride containing 10% of methanol. The organic extracts were washed with water, dried and evaporated to dryness to obtain 9 g of raw product. The latter was crystallized from ether to obtain 5 g of product which was dissolved in 10 ml of refluxing methanol. 100 ml of methylene chloride were added to the mixture which was then concentrated to 30 to 40 ml. Crystallization was induced and the mixture was held overnight in the refrigerator and was then vacuum filtered. The recovered product was washed with methylene chloride and was dried at 80° C. under reduced pressure to obtain 3 g of 3,3'-(propylimino-di-2,1-ethanediyl)-bis-phenol in the form of colorless crystals metling at 125° C.

| Analysis: $C_{19}H_{25}NO_2$; molecular weight = 299.4 | | | |
|---|---|---|---|
| Calculated: | % C 76.22 | % H 8.42 | % N 4.68 |
| Found: | 76.0 | 8.4 | 4.4 |

EXAMPLE 5

Fumarate of diacetate of 3,3'-(propylimino di-2,1-ethanediyl)-bis-phenol 0.7 ml of acetyl chloride were added under nitrogen at 20°–25° C. to a solution of 690 mg of the bis-phenol of Example 4 in 2.8 ml of trifluoroacetic acid and the mixture was stirred for 15 minutes and was then evaporated to dryness under reduced pressure at 30° C. The residue was dissolved in ethyl acetate and the solution was washed with dilute sodium bicarbonate solution, then with water, dried and evaporated to dryness to obtain 800 mg of the diacetate of 3,3'-(propylimino-di-2,1-ethanediyl)-bis-phenol in the form of a yellow oil.

10 ml of ethyl acetate were added at 50° C. to a solution of 750 mg of the said product, 220 mg of fumaric acid and 3 ml of methanol and the mixture was filtered and concentrated to 3 ml. Crystallization was induced and the mixture stood overnight in a refrigerator. The mixture was vacuum filtered and the recovered product was washed with ethyl acetate and dried to obtain 900 mg of product. The latter was crystallized from ethyl acetate to obtain 850 mg of the fumarate of the diacetate of 3,3'-(propylimino-di-2,1-ethanediyl)-bis-phenol in the form of colorless crystals melting at about 110° C.

| Analysis: $C_{23}H_{29}NO_4 \cdot C_4H_4O_4$; molecular weight = 499.57 | | | |
|---|---|---|---|
| Calculated: | % C 64.91 | % H 6.66 | % N 2.80 |
| Found: | 64.7 | 6.8 | 2.7 |

EXAMPLE 6

Tablets were prepared containing 25 mg of 3-[2-{N-phenethyl) (N-propyl)-amino}-ethyl]-phenol hydrochloride or 3,3'-(propylimino-di-2,1-ethanediyl)-bis-phenol and sufficient excipient of lactose, starch, talc and magnesium stearate to obtain a final tablet weight of 200 mg.

PHARMACOLOGICAL STUDY

A. Rotation after unilateral injury to nigrostriated fasciculus with 6-hydroxydopamine The test was conducted on groups of 6 male rats weighing about 250 g and the injury was caused by injection in the dark substance of 8 μg of 6-hydroxydopamine hydrochloride dissolved in 4 μl of physiological serum containing 1 mg/ml of ascorbic acid [U Ungerstedt, Acta physiol. Scand., Vol. 82 (1971), supp. 367, p. 69–93]. The test compounds were administered orally or intraperitoneally and the animals were individually placed in a rotometer which counted the number of rotations of each animal in 2 ways. Each test lasted for 90 minutes and under these conditions, the compounds of Examples 1, 2 and 4 showed contralateral rotations at a dose of 10 mg/kg after oral and intraperitoneal administration. These results show that the tested compounds possess interesting dopaminergic stimulating activity.

B. Acute toxicity

The 50% lethal dose ($DL_{50}$) was determined for the products after intraperitoneal administration to mice and the mortality was determined 48 hours after the administration of the test product. The $DL_{50}$ for products of Examples 1, 2, 3 and 4 was 100, 150, 350 and 300 mg/kg, respectively.

Various modifications of the products and methods of the invention may be made without departing from the spirit or scope thereof and it is to be understood that the invention is to be limited only as defined in the appended claims.

We claim:
1. A compound selected from the group consisting of phenethylamines of the formula

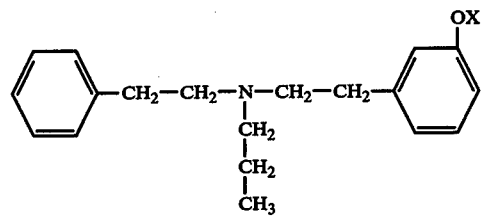

wherein X is selected from the group consisting of hydrogen, acyl of an aliphatic carboxylic acid of 2 to 6 carbon atoms and benzoyl and Y is selected from the group consisting of hydrogen and —OX and their non-toxic, pharmaceutically acceptable acid addition salts.
2. A compound of claim 1 wherein Y is hydrogen.
3. A compound of claim 1 wherein when Y is hydroxy, X is hydrogen, when Y is acetoxy, X is acetyl and when Y is benzoyloxy, X is benzoyl.
4. A compound of claim 1 wherein Y is hydrogen and X is selected from the group consisting of hydrogen, acetyl and benzoyl.
5. A compound of claim 1 selected from the group consisting of 3-[2-{(N-phenethyl) (N-propyl)-amino}-ethyl]-phenol and its hydrochloride.
6. A compound of claim 1 selected from the group consisting of the acetate of 3-[2-{(N-phenethyl) (N-propyl)-amino}-ethyl]-phenol and its hydrochloride.

7. A compound of claim 1 selected from the group consisting of the benzoate of 3-[2-{(N-phenethyl) (N-propyl) amino}-ethyl]-phenol and its monofumarate.

8. A compound of claim 1 which is 3,3'-(propyliminodi-2,1-ethanediyl)-bis-phenol.

9. A compound of claim 1 selected from the group consisting of the diacetate of 3,3'-(propyliminodi-2,1-ethanediyl)-bis-phenol and its monofumarate.

10. A process for the preparation of a compound of claim 1 comprising hydrolyzing a compound of the formula

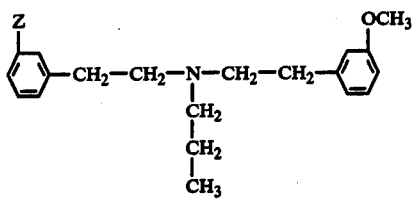

wherein Z is hydrogen or methoxy to obtain a compound of the formula

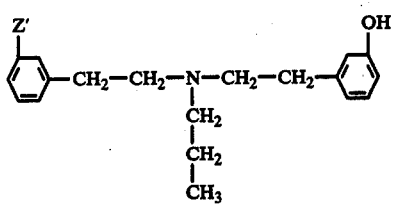

wherein Z' is hydrogen or hydroxy which may be isolated and if desired salified or may be reacted with an acid halide of the formula X'—Hal wherein X' is benzoyl or acyl of an aliphatic carboxylic acid of 2 to 6 carbon atoms or with an acid anhydride of the formula (X')$_2$O to obtain a compound of the formula

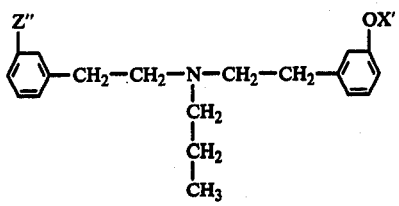

wherein X' has the above definition and Z" is hydrogen or OX' which, if desired may be salified.

11. The process of claim 10 wherein Y, Z, Z' and Z" are hydrogen.

12. The compound of the formula

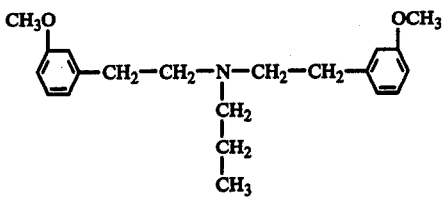

13. A dopaminergic composition comprising a dopaminergically effective amount of at least one compound of claim 1 and an inert pharmaceutical carrier.

14. The composition of claim 13 wherein Y is hydrogen.

15. The composition of claim 13 wherein when Y is hydroxy, X is hydrogen, when Y is acetoxy, X is acetyl and when Y is benzoyloxy, X is benzoyl.

16. The composition of claim 13 wherein Y is hydrogen and X is selected from the group consisting of hydrogen, acetyl and benzoyl.

17. A method of treating the syndromes of Parkinson disease in human comprising administering to humans a dopaminergically effective amount of at least one compound of claim 1.

18. The method of claim 17 wherein Y is hydrogen.

19. The method of claim 17 wherein Y is hydroxy, X is hydrogen, when Y is acetoxy, X is acetyl and when Y is benzoyloxy, X is benzoyl.

20. The method of claim 17 wherein Y is hydrogen and X is selected from the group consisting of hydrogen, acetyl and benzoyl.

21. A method of inducing dopaminergic stimulating activity in warm-blooded animals comprising administering to warm-blooded animals a dopaminergically effective amount of at least one compound of claim 1.

* * * * *

UNITED STATES PATENT OFFICE
CERTIFICATE OF CORRECTION

Patent No. 4,130,658  Dated Dec. 19, 1978

Inventor(s) LUCIEN NEDELEC, DANIEL FRECHET and CLAUDE DUMONT

It is certified that error appears in the above-identified patent and that said Letters Patent are hereby corrected as shown below:

Column 8, Claim 1, 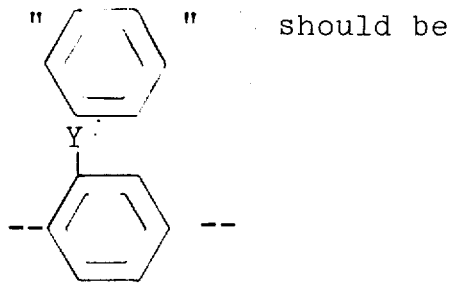 should be

Signed and Sealed this

*Seventh* Day of *August 1979*

[SEAL]

Attest:

Attesting Officer

LUTRELLE F. PARKER
*Acting Commissioner of Patents and Trademarks*